(12) United States Patent
Regier et al.

(10) Patent No.: US 6,643,593 B2
(45) Date of Patent: Nov. 4, 2003

(54) METHOD, DEVICE AND COMPUTER-READABLE MEMORY CONTAINING A COMPUTER PROGRAM FOR DETERMINING AT LEAST ONE PROPERTY OF A TEST EMULSION AND/OR TEST SUSPENSION

(75) Inventors: Marc Regier, Karlsruhe (DE); Helmar Schubert, Carl-Hofer-Strasse 1A, 76227 Karlsruhe (DE); Thomas Danner, Karlsruhe (DE)

(73) Assignees: Universitat Karlsruhe (DE); Helmar Schubert (DE)

( * ) Notice: Subject to any disclaimer, the term of this patent is extended or adjusted under 35 U.S.C. 154(b) by 0 days.

(21) Appl. No.: 09/898,116

(22) Filed: Jul. 3, 2001

(65) Prior Publication Data

US 2002/0032534 A1 Mar. 14, 2002

(51) Int. Cl.⁷ .................... G01N 33/543; G06F 19/00
(52) U.S. Cl. ................... 702/57; 435/6; 435/7.21; 702/127
(58) Field of Search ............................ 324/665; 702/57, 702/58, 84, 127, 130, 136, 137; 435/6, 7.21; 436/518; 438/1; 600/547

(56) References Cited

U.S. PATENT DOCUMENTS 5,541,072 A  *  7/1996  Wang et al. ............... 435/7.21
5,891,630 A  *  4/1999  Eggers et al. .................. 435/6

* cited by examiner

*Primary Examiner*—John Barlow
*Assistant Examiner*—John Le
(74) *Attorney, Agent, or Firm*—Anthony J. Casella; Gerald E. Hespos

(57) ABSTRACT

A method, a device and a computer-readable memory having a computer program stored thereon are provided for determining at least one property of a test emulsion and/or test suspension and/or of a test foam as a test substance, wherein the property influences the dielectric constant of the test substance and is different than it. The method includes preparing a test substance to be studied; establishing the real and/or imaginary part(s) of the dielectric constant of the test substance at at least one frequency; and determining the at least one property of the test substance by using the established real and/or imaginary part(s).

18 Claims, 11 Drawing Sheets

| EIGENVALUE # | $\varepsilon'$ | $\varepsilon''$ |
|---|---|---|
| 1 | 2533922.858 | 285725.056 |
| 2 | 593.187 | 17.304 |
| 3 | 6.055 | 7.793 |
| 4 | 2.783 | 2.682 |
| 5 | 1.382 | 1.031 |
| 6 | 0.518 | 0.446 |
| 7 | 0.229 | 0.142 |
| 8 | 0.090 | 0.073 |
| 9 | 0.013 | 0.015 |

METHOD, DEVICE AND COMPUTER-READABLE MEMORY CONTAINING A COMPUTER PROGRAM FOR DETERMINING AT LEAST ONE PROPERTY OF A TEST EMULSION AND/OR TEST SUSPENSION

BACKGROUND OF THE INVENTION

1. Field of the Invention

The invention relates to a method for determining at least one property of a test substance, a device for determining at least one property of a test substance, the use of this device and a computer-readable memory containing a computer program for determining at least one property of a test substance.

2. Description of the Related Art

Emulsions are disperse systems of two liquids, or phases, that are immiscible or only partially miscible with one another, one of which is finely divided in the other. Accordingly, they comprise an inner, or disperse, phase and an outer, or continuous, phase, with the inner phase being the fraction of the system that is typically present in small droplets. The term suspensions is used to mean disperse systems in which a solid substance is finely divided in a liquid substance. The term foam is used to mean a disperse distribution of gas-filled bubbles in a liquid and/or solid medium, which is created e.g. by vigorous impact, shaking, spraying, stirring and/or chemical reactions. Emulsions and suspensions, as well as foams, are very important in many fields of industrial, health and household technology, for example for food, cosmetics, pharmaceuticals and dyes. Owing to this, there is significant interest in methods and devices for the quality control and characterization of emulsions and suspensions. Particularly important properties of emulsions, which are directly related to their quality, are the volume ratio of the two phases as well as the drop size, or the drop size distribution, of the drops in the disperse phase of the emulsion.

To determine the volume ratios of the disperse and continuous phases of emulsions, it is customary to use the density of the emulsion. Furthermore, the volume ratio can also be obtained from final drying of the emulsion. However, such determination of the volume ratio by measuring the density of the components that are used is successful only if two pure components are present, or if the precise composition of the respective components is known at any time. The same limitations with respect to the possible compositions of the emulsions also exist for said method involving final drying and weighing of the emulsions. Drying analysis is also time-consuming, and cannot therefore be used as an in-situ, or in-line, method during the emulsification process. In order to determine the drop size, or the drop size distribution, of the disperse phase, it is customary to use laser diffraction spectrometry or ultrasound extinction experiments. For in-line monitoring, fiber optic sensors are used. In this case, however, the drop size determination is restricted to low-concentration emulsions. Furthermore, said fiber optic sensors can only be used to determine the specific surface area of the disperse phase, and therefore merely an average drop size—but not the drop size distribution.

It is an object of the invention to provide a simple, cost-effective and fast method for determining properties of emulsions and/or suspensions and/or foams, which can preferably also be used as an in-line method during the production of the emulsion and/or suspension or immediately following its production. It is also an object of the invention to provide a corresponding device and a corresponding computer-readable storage medium having a computer program stored thereon for determining properties of emulsions and/or suspensions and/or foams.

SUMMARY OF THE INVENTION

According to the method according to the invention, properties of test substances, which comprise test emulsions and/or test suspensions and/or test foams, are determined insofar as these properties have an influence on the dielectric properties of the test substance. In this case, the term emulsions is used to mean disperse systems of two liquids, or phases, that are immiscible or only partially miscible with one another, one of which is finely divided in the other. An emulsion therefore comprises an inner, or disperse, phase and an outer, or continuous, phase, with the inner phase being the fraction of the system that is typically present in small droplets. Conversely, the term suspensions is used to mean disperse systems in which a solid substance is finely divided in a liquid substance. The term foam, or spumoid, is used to mean a disperse distribution of gas-filled bubbles or pores or cells in a liquid and/or solid medium, which is created e.g. by vigorous impact, shaking, spraying, stirring and/or chemical reactions. Furthermore, the property in question should not be the same as the dielectric properties of the test substance, but should merely represent a property that influences the dielectric properties, i.e. is not independent of them. Surprisingly, such properties of a test substance can be determined from its dielectric properties. In this case, the real or imaginary part of the complex dielectric constant of the test substance is sufficient, said part being established at one frequency, typically by a measurement. An advantageous, in particular redundant, determination is possible if both the real part and the imaginary part of the dielectric constant are established. It is also conceivable to establish the dielectric constant of the test substance by means of an impedance measurement.

According to the invention, the real and/or imaginary part(s) of the dielectric constant of the test substance is established at a plurality of frequencies, i.e. at two or more. Accordingly, an (optionally complex) dielectric spectrum of the test substance is used, although just the real or the imaginary part of the dielectric constant is typically sufficient for determining the test substance property in question. An advantageous, in particular redundant, determination is possible if both the real part and the imaginary part of the dielectric constant is spectroscopically recorded.

According to a preferred embodiment of the invention, the test substance properties to be determined are determined with the assistance of at least one real and/or imaginary part of the dielectric constant of at least one reference emulsion and/or of at least one reference suspension and/or of at least one reference foam as at least one reference substance, in which the at least one property to be determined is known. The reference suspension, which may be a reference emulsion and/or a reference suspension, is typically a substance that is very similar to or corresponds to the test substance, but in which the property in question, i.e. the material parameter in question, is known. From the real and/or imaginary part(s) of the dielectric constant of such a reference substance, in conjunction with the aforementioned method, it is possible to determine the test substance property in question. Typically, the real and/or imaginary part(s) of the dielectric constant of the reference substance at that frequency or those frequencies at which the real and/or imaginary part(s) of the dielectric constant of the test substance has been established, is used for the determination.

According to another embodiment, the method according to the invention comprises the further steps of preparing the at least one reference substance; and establishing the real and/or imaginary part(s) of the dielectric constant of the reference substance at at least one or a plurality of frequencies.

This makes it possible, even without the assistance of, for example, collections of material properties or data sheets, to use reference substances whose property in question—but not its dielectric constant—is known. The steps of establishing the real and/or imaginary part(s) of the dielectric constant of the reference substance are therefore used to compile reference data that are preferably used to calibrate the actual method of determining the property of the test substance.

Preferably, the real and/or imaginary part(s) of the dielectric constants of the at least one reference substance is established at a plurality of frequencies (two or more), i.e. a spectrum of the (complex) dielectric constants of the at least one reference substance is used. Using spectra of the dielectric constants of the reference substance (and of the test substance) has the advantage that the method according to the invention can even be used to determine properties of the test substance which, although they could not be determined from the dielectric constant at a single frequency, could be determined from a spectrum thereof.

According to another embodiment of the invention, a plurality of reference substances are prepared, which differ from one another and from the test substance at most in terms of the at least one property to be determined and consequent properties related thereto. For example, the reference substances form a substance series in which a particular property of the reference substance, for example the volume ratio of the disperse and continuous phases, is varied while all the other material parameters remain unchanged. Merely properties, or parameters, which necessarily also change in the event of a change in the property to be determined, i.e. so-called dependent consequent properties, also differ between the reference substances. An example of such a plurality of reference substances are reference emulsions that differ from one another merely by the volume ratio of the disperse and continuous phases, and otherwise correspond to the test emulsion. The unknown volume ratio of the test emulsion can therefore be determined in a straightforward way. If, for instance, the average drop size of a test emulsion is to be determined, then a test substance series that matches the test emulsion except for different average drop sizes, could be chosen as the plurality of reference substances.

The frequencies at which the (complex) dielectric constant is established preferably lie in a range of from 1 MHz to 20 GHz, preferably from 200 MHz to 6 GHz.

According to a particularly preferred embodiment of the invention, m reference substances $S_1, \ldots, S_m$ having assigned known properties $\phi_1, \ldots, \phi_m$ are prepared and the method comprises the further steps of establishing the real $\epsilon'(\phi_i, f_j)$ and/or imaginary part(s) $\epsilon''(\phi_i, f_j)$ of the dielectric constant of each of the reference substances $S_1, \ldots, S_m$ at n different frequencies $f_1, \ldots, f_n$; forming a data matrix $D' = (\epsilon'(\phi_i, f_j))_{1 \leq i \leq m; 1 \leq j \leq n}$ and/or a data matrix $D'' = (\epsilon''(\phi_i, f_j))_{1 \leq i \leq m; 1 \leq j \leq n}$ having m columns and n rows; the property of the test substance being determined with the assistance of the data matrix $D' = (\epsilon'(\phi_i, f_j))_{1 \leq i \leq m; 1 \leq j \leq n}$ and/or $D'' = (\epsilon''(\phi_i, f_j))_{1 \leq i \leq m; 1 \leq j \leq n}$.

The data matrix D or D' consequently contains, as entries, the real or imaginary parts, respectively, of the dielectric constants of the reference substances at a particular frequency. For instance, the matrix element of the column i and cell j in the data matrix D' or D" is the real or imaginary part, respectively, of the dielectric constants of the reference substance i, which has the property $\phi_i$ at, specifically, the frequency $f_j$.

According to a particularly preferred embodiment, the method further comprises a steps of performing a principal component analysis of the data matrix $D' = R' \times C'$ to calculate the principal component matrix R' and the weighting matrix C' of the data matrix D' and/or performing a principal component analysis of the data matrix $D'' = R'' \times C''$ to calculate the principal component matrix R" and the weighting matrix C" of the data matrix D". The method proceeds by calculating the correlation between the weighting of at least the first principal component of the principal component matrix R' and/or R" and the properties $\phi_1, \ldots, \phi_m$ of the reference substances $S_1, \ldots, S_m$; and establishing the real $\epsilon'(\phi_{test}, f_j)$ and/or imaginary part(s) $\epsilon''(\phi_{test}, f_j)$ of the dielectric constant of the test substance $S_{test}$ at the n different frequencies $f_1, \ldots, f_n$. The method continues by calculating a weighting that is required for the at least first principal component of the principal component matrix R' and/or R" to reproduce $\epsilon'(\phi_{test}, f_j)$ and/or $\epsilon''(\phi_{test}, f_i)$, and determining the property $\phi_{test}$ of the test substance from the calculated required weighting with the aid of the calculated correlation.

Such a principal component analysis (PCA) is particularly advantageous for very large data records, i.e. in cases in which the (m,n) data matrix has many entries. Principal component analysis is a known statistical tool, and has been applied successfully to physical and chemical problems for more than 30 years. In this context, reference may be made to, for example, the book by Malinowsky, I. R., Howery, D. G., 1980, Factor Analysis In Chemistry, J. Wiley & Sons, which describes the method of principal component analysis in detail. The purpose of principal component analysis is, from a large data record of measurement points, to determine the principal components and the associated weightings of these principal components for each individual measured spectrum.

Principal component analysis involves splitting the data matrix D or D" into two matrices, specifically R' or R" and the matrix of the associated weightings C' or C", respectively. In this case, values suffixed by a single prime are assigned to the real part and values suffixed by a double prime are assigned to the imaginary part of the dielectric constant. The principal component matrix R' or R" and the weighting matrix C' or C" are determined by means of principal component analysis in the known way. To that end, in particular, the covariance matrix $Z = D \times D^T$ may firstly be calculated from the product of the data matrix with its transpose. The principal component matrix R is then given as the product of the data matrix D with a matrix Q, which is the sorted eigenvector matrix of the covariance matrix Z. The weighting matrix C can be determined from the transposed eigenvector matrix.

Typically, only a few principal components of the principal component matrix R with associated weightings are needed for a sufficiently accurate description of the dielectric spectra of the reference substances. In many cases, even a single principal component is sufficient. A correlation is then calculated between the weighting of the first (most important) principal component of the principal component matrix R and the known properties $\phi_i$ of the reference substances $S_i$, i.e. the value that the weighting of the first principal component must have in order to describe the spectrum of the respective reference substance $S_i$ with the properties $\phi_i$ is determined. In order then to study an (unknown) test substance with respect to the property to be determined, its dielectric spectrum is established and the weighting that is required for the at least first principal component of the principal component matrix R to reproduce this spectrum is calculated. The property $\phi_{test}$ of the test substance can be determined from this required weighting with the aid of the previously calculated correlation. In particular, spline interpolations are highly suitable for the required correlation.

According to another preferred embodiment, the property of the test substance is determined during and/or immediately following the production thereof and can, in particular, be used to control, regulate and/or monitor the production process of the test substance. A particular advantage of the method according to the invention is that it is suitable as an in-situ, or in-line, method. Determination of interesting properties of the test substance can therefore be performed actually during the production of the test substance (an emulsion or a suspension or a foam). The test substance properties determined in this way can be used, on the one hand, to monitor the production process, for example with respect to production tolerances. On the other hand, the test substance properties obtained in this way can also be used for controlling or regulating the production method of the test substance, i.e. there may be active feedback of the properties of the test substance that has just been produced into the production process.

The method according to the invention can be used particularly preferably to determine the volume ratios between disperse and continuous phases, the drop size distribution of the disperse phase, the average drop size of the disperse phase, the average size of the foam bubbles or cells or pores and/or the viscosity of the test substance. Nevertheless, the method according to the invention can also be used with a large number of other important properties, or parameters, of emulsions and suspensions and foams.

According to the invention, a device for determining at least one property of a test emulsion and/or test suspension and/or of a test foam as a test substance, the property influencing the dielectric constant of the test substance and being different than it, comprises at least one measuring device for establishing the real and/or imaginary part of the dielectric constant of the test substance at a plurality of frequencies and an evaluation device that determines the at least one property of the test substance by using the established real and/or imaginary part(s). The device can therefore be used to determine all properties of test substances, which are test emulsions and/or test suspensions, that have an influence on their dielectric properties. The property in question is determined by means of an evaluation device while using the real and/or imaginary part(s) of the dielectric constant of the test substance at at least two frequencies.

Preferably, the evaluation device determines the at least one property of the test substance with the assistance of at least one real and/or imaginary part of the dielectric constant of at least one reference emulsion and/or of at least one reference suspension and/or of at least one reference foam as at least one reference substance, in which the at least one property to be determined is known. Besides the established dielectric constant of the test substance, the evaluation device therefore also takes into account the real and/or imaginary part(s) of the dielectric constant of at least one reference substance, which may be a reference emulsion and/or a reference suspension, when determining the property of the test substance.

According to a preferred embodiment of the invention, the measuring device is designed to establish the real and/or imaginary part(s) of the dielectric constant of the at least one reference substance. This also makes it possible to use reference substances which, although they are known with respect to the property in question, nevertheless have unknown dielectric properties.

According to a particularly preferred embodiment, the measuring device comprises a network analyzer with an attached dielectric measuring head, which is preferably designed to establish the real and/or imaginary part(s) of the dielectric constants of the test and, preferably, reference substances in a frequency range of from 1 MHz to 20 GHz, in particular from 200 MHz to 6 GHz. In this context, conventional instruments may be used as network analyzers and/or dielectric measurement systems.

According to a particularly preferred embodiment of the invention, the evaluation device and a substance production device that produces the test substance are in signal communication with a control device, and the control device is designed to control, regulate and/or monitor the substance production device while taking into account the test substance property determined by the evaluation device. This makes it possible to use the device in the scope of the production process of the test substance for in-situ, or in-line, characterization of the test substance property in question. This may be advantageous, on the one hand, for quality-assurance monitoring of a critical property of the test substance, but also for active feedback of the determined properties of the test substance into the substance production device.

The invention also proposes the use of an above-described device according to the invention for determining the volume ratio between disperse and continuous phases, the drop size distribution of the disperse phase, the average drop size of the disperse phase, the average size of the foam bubbles or cells or pores and/or the viscosity of the test substance.

According to the invention, a computer-readable storage medium comprises a computer program stored thereon for determining at least one property of a test emulsion and/or test suspension and/or of a test foam as a test substance, the property influencing the dielectric constant of the test substance and being different than it, which has program parts for recording the real and/or imaginary part(s) of the dielectric constant of the test substance at a plurality of (two or more) frequencies and for determining the at least one property of the test substance by using the established real and/or imaginary part(s). The computer program product is therefore designed to determine properties that affect the complex dielectric function of a test substance, i.e. of a test emulsion and/or test suspension.

According to a preferred embodiment, the property of the test substance is determined with the assistance of at least one real and/or imaginary part of at least one reference emulsion and/or of at least one reference suspension and/or of at least one reference foam as at least one reference substance, in which the at least one property to be determined is known.

The invention will be described by way of example below with reference to the drawings.

BRIEF DESCRIPTION OF THE DRAWINGS

FIG. 3b shows a dielectric spectrum ε"(f) of the various reference emulsions in FIG. 3a.

FIG. 4 shows a table with calculated eigenvalues of the covariance matrix Z of the data matrix D.

DETAILED DESCRIPTION OF THE PREFERRED EMBODIMENT

Figure 1:
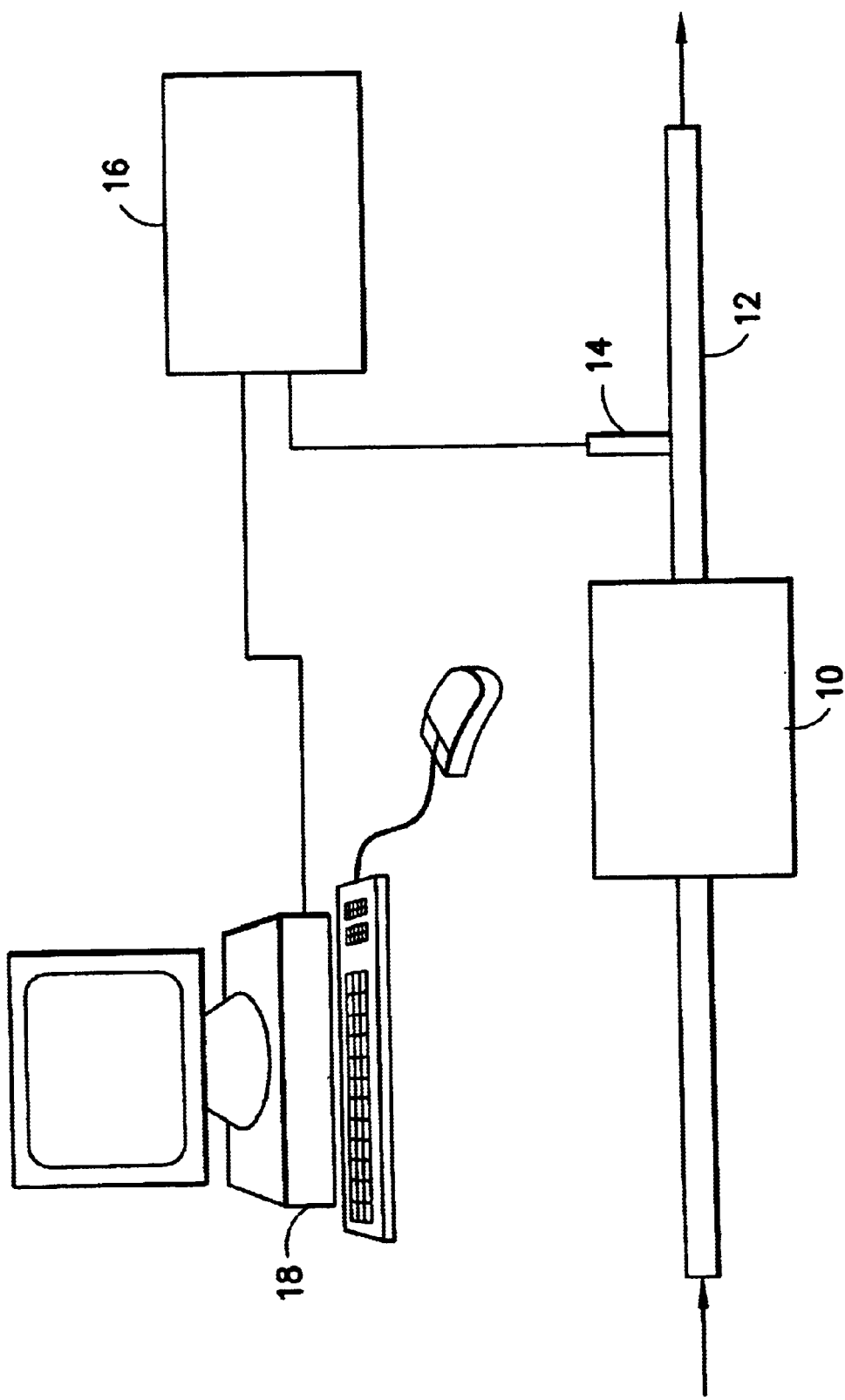
FIG. 1 shows a schematic structure of a measurement system according to one embodiment of the invention.

FIG. 1 shows the schematic structure of an embodiment of a device for determining at least one property of a test emulsion. In the same way, this structure could also be used to determine at least one property of a test suspension, of a test foam or even of a test substance that represents a mixture of an emulsion, a suspension and/or a foam. The device comprises an emulsifier unit 10, which is used as a substance production device. A raw emulsion is introduced into the emulsifier unit 10 and—after processing has been completed—is delivered as a fine emulsion. A dielectric probe head 14 is arranged, in the output channel 12 of the emulsifier unit 10, in such a way that the fine emulsion that is produced (or a fine suspension, respectively) is in direct contact with it or immersed in it. The dielectric probe head 14 is connected to a network analyzer 16 via a coaxial line.

Figure 2:
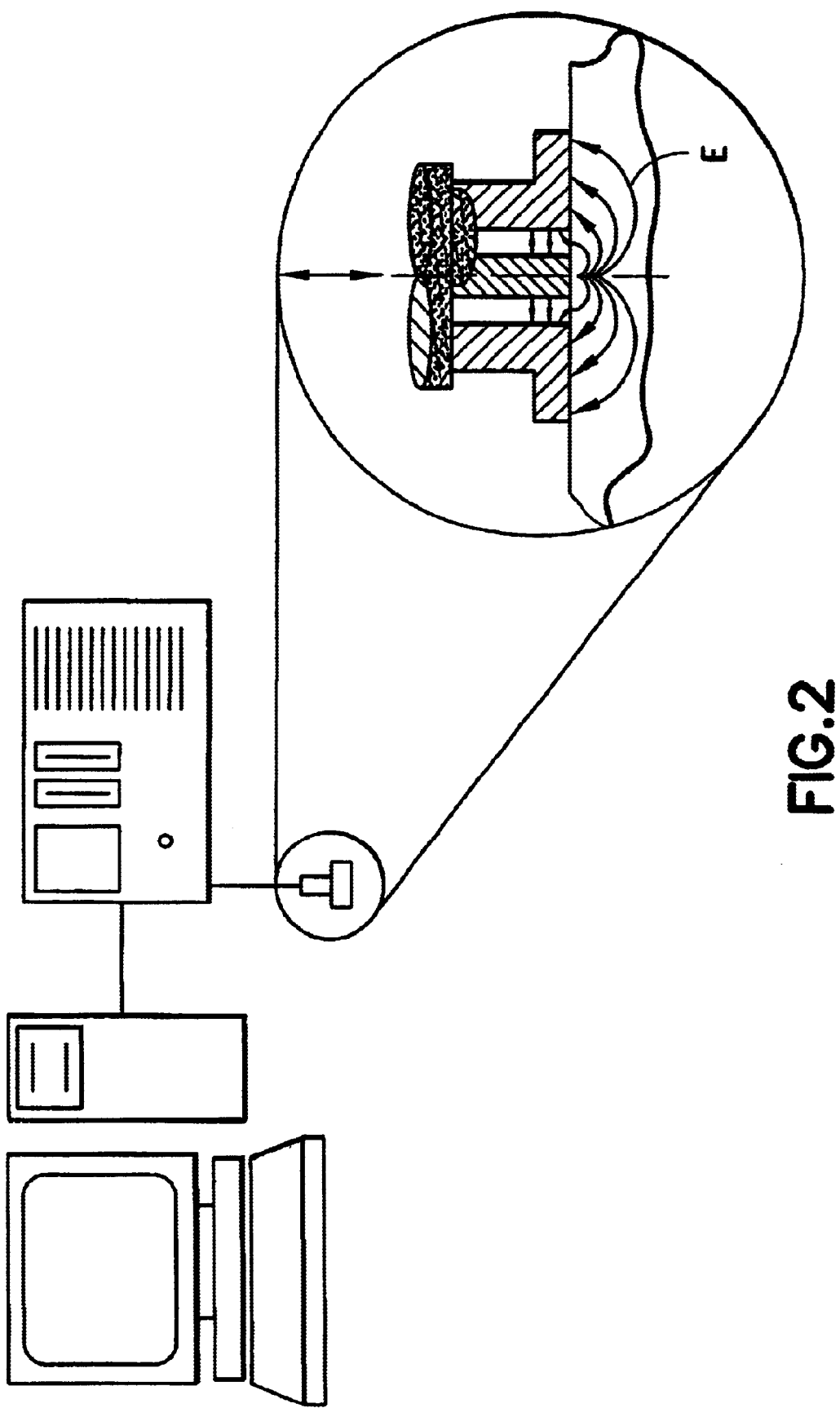
FIG. 2 shows a schematic detail of the measurement system shown in FIG. 1 with a detailed view of the dielectric probe head.

An enlarged detailed view of the dielectric probe head 14 is represented in FIG. 2. The measurement principle for determining the (complex) dielectric constant of the substance, i.e. of the fine emulsion or fine suspension that is produced, or of the fine foam, is based on the open coaxial line principle. The dielectric probe head comprises an open end of the coaxial line leading to the network analyzer 16, with the electric field lines between an inner conductor of the coaxial line and its outer conductor at the open end lying partially in a region of space that is taken up operationally by the substance to be studied. The dielectric properties of this substance therefore influence the electromagnetic state at the open end of the coaxial line. Changes in this electromagnetic state at the dielectric probe head 14 can be detected by the network analyzer 16, so that it is possible to measure the dielectric properties. It is also conceivable to determine the relevant property with the aid of an impedance measurement.

The dielectric probe head 14, together with the network analyzer 16, forms a measuring device. Furthermore, the network analyzer 16 is connected to a computer 18 that serves as an evaluation device. The computer 18 processes the dielectric properties established by the measuring device for the substances being studied and, after evaluation and processing have been carried out, it delivers the result of the test substance property to be determined.

The method according to the invention and the device according to the invention will be described below in the context of an example, in which the volume ratio between disperse and continuous phases of an oil-in-water emulsion is determined. The oil-in-water (O/W) emulsions were produced in an ultrasound batch process by using the emulsifier unit 10. An aqueous emulsifier solution (5 g/l LEO-10) and vegetable oil were used as the basic substance. A 70% by volume O/W emulsion was produced by an ultrasound power input of $P/V=4\times10^4$ W/m$^3$ with a duration of 20 minutes. The average drop size was established using a laser diffractometer, and was approximately 5 µm. Less concentrated reference, or calibration, emulsions were produced from this concentrated basic emulsion by diluting with water. It was therefore possible to ensure that the drop size distribution remained constant between the reference emulsions. The reference emulsions that were produced differed from one another merely in terms of their differing oil concentration.

Figure 3A:
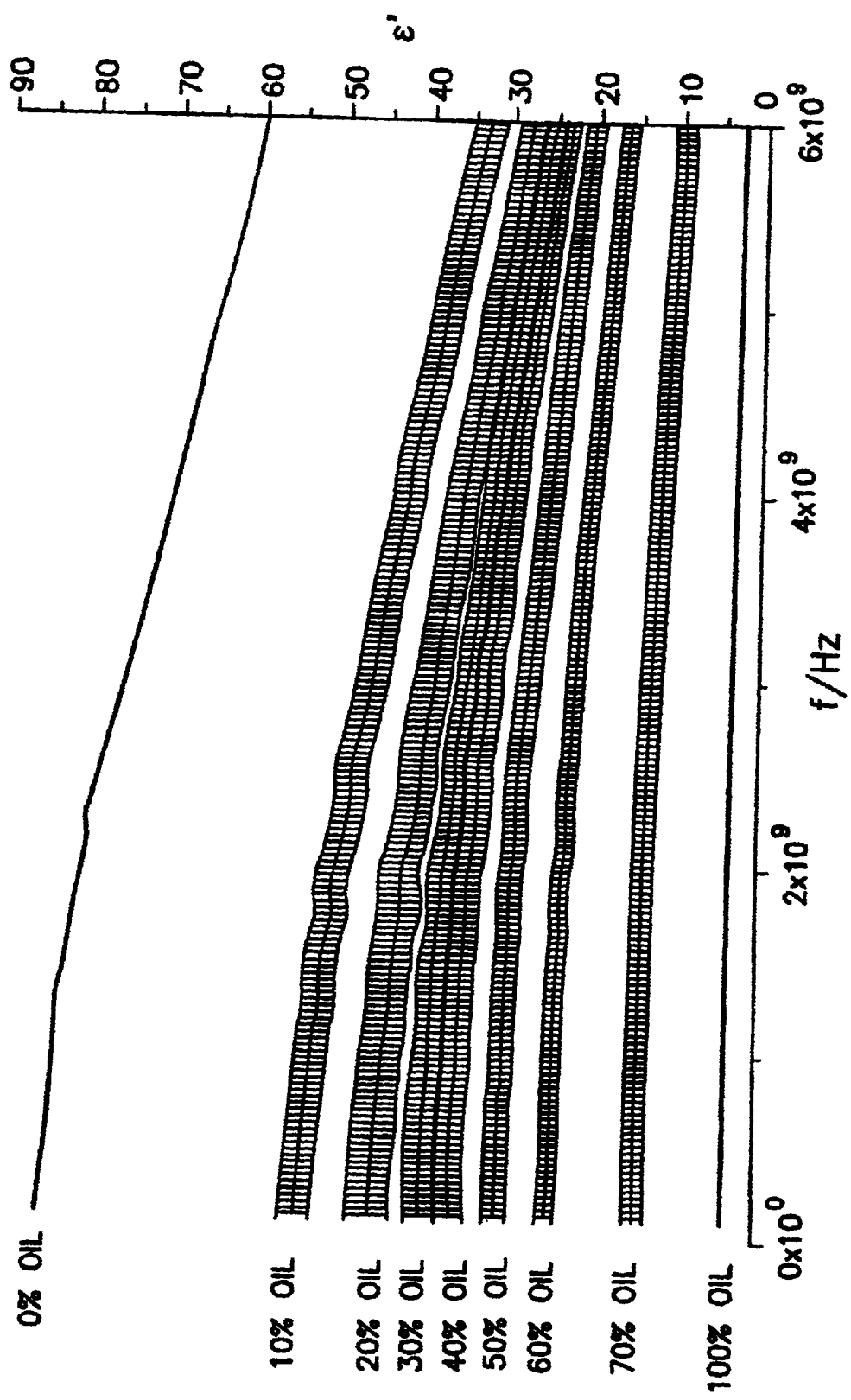
FIG. 3a shows a dielectric spectrum $\epsilon'(f)$ of various reference emulsions.
Figure 3B:
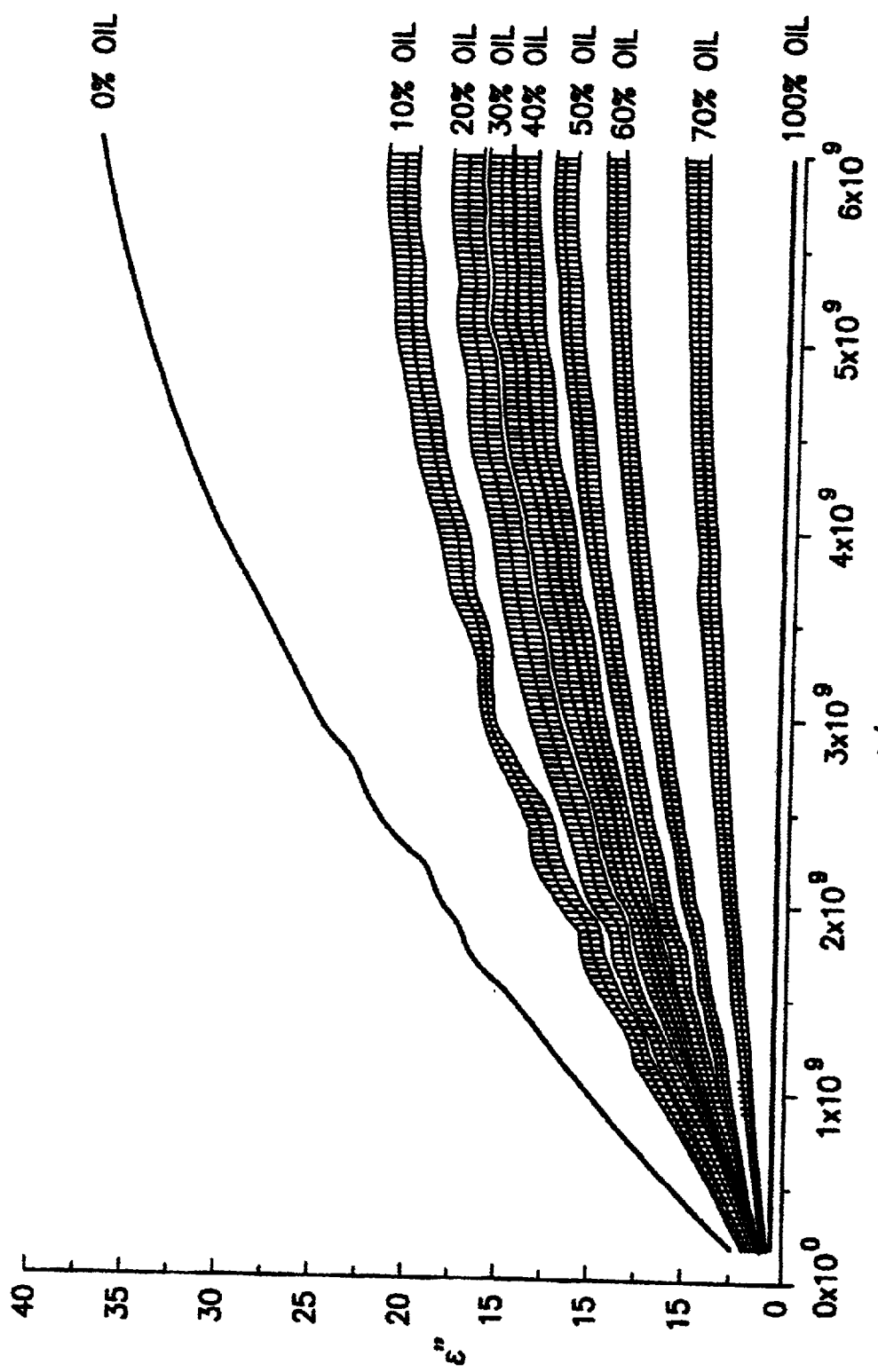

The dielectric properties, i.e. the real and imaginary parts of the dielectric constants of the reference emulsions that were produced were measured using the dielectric probe head 14 (for example a Hewlett-Packard 85070B) and the network analyzer 16 (for example a Hewlett-Packard 8753D) over a frequency range of from 0.2 to 6 GHz in 200 frequency steps. FIG. 3a shows the result of the measurement of the real part of the dielectric constant of the reference emulsions that were produced, as a function of frequency. Besides the seven reference emulsions (oil volume ratio from 10% to 70%), the real part ε'(f) of the dielectric constants for pure oil and pure water are also shown. FIG. 3b shows, for the same frequency range, the measured imaginary part ε"(f) of the dielectric constants for the nine different reference substances. The standard deviations of each three successive measurements have been plotted as error bars in FIGS. 3a and 3b.

The measurement process, divided into 200 frequency steps, for the dielectric constant of the reference substances provides discretized spectra ε'(f) and ε"(f) as a reference database. This comparatively large data set was subjected, for further processing, to principal component analysis (PCA). It is, however, equally possible to establish the test substance properties in question directly from the discretized dielectric spectra of the reference substances. To perform the principal component analysis, data matrices [D'] and [D"] are defined which have, as entries, the real (ε') and imaginary (ε") parts, respectively, of the dielectric constants of the various reference emulsions at the various measurement frequencies. The following equation applies: where $\epsilon'(\phi_i, f_j)$ is the value of the dielectric constant (real or imaginary part, respectively) at the oil concentration $\phi_i$ and at the frequency $f_j$. In principle, it is possible to work either with the real part ε' or with the imaginary part ε", or even a combination of the two components of the dielectric constant. In the following example, merely the imaginary part ε" was evaluated, i.e. the data matrix [D"] (hereafter simply referred to as [D]) was evaluated. In the scope of the principal component analysis, the data matrix [D] is split into a product of two matrices, specifically the principal component matrix [R] and the weighting matrix [C], so that the equation [D]=[R]×[C] applies. The principal component matrix [R] is given as the product of the data matrix [D] with a matrix [Q], which is the sorted eigenvector matrix of a covariance matrix [Z]= [C]×[D]$^T$. [D]$^T$ denotes the transpose of the data matrix [D]. The weighting matrix [C] can be determined from the transposed eigenvector matrix.

Figure 5:
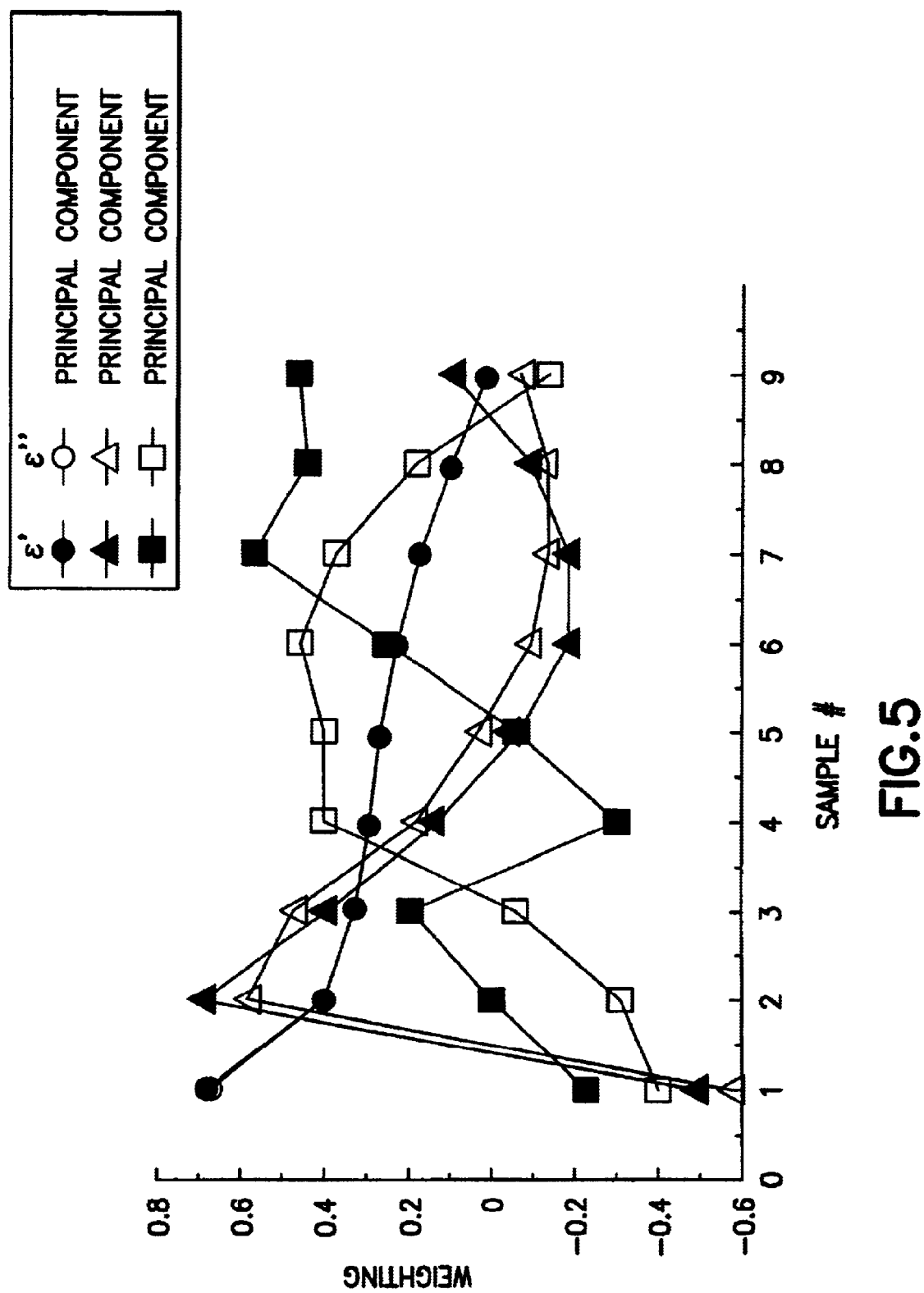
FIG. 5 shows a diagram that shows the weightings of the first three basis vectors as a function of the sample number of the reference emulsion.
Figure 6:
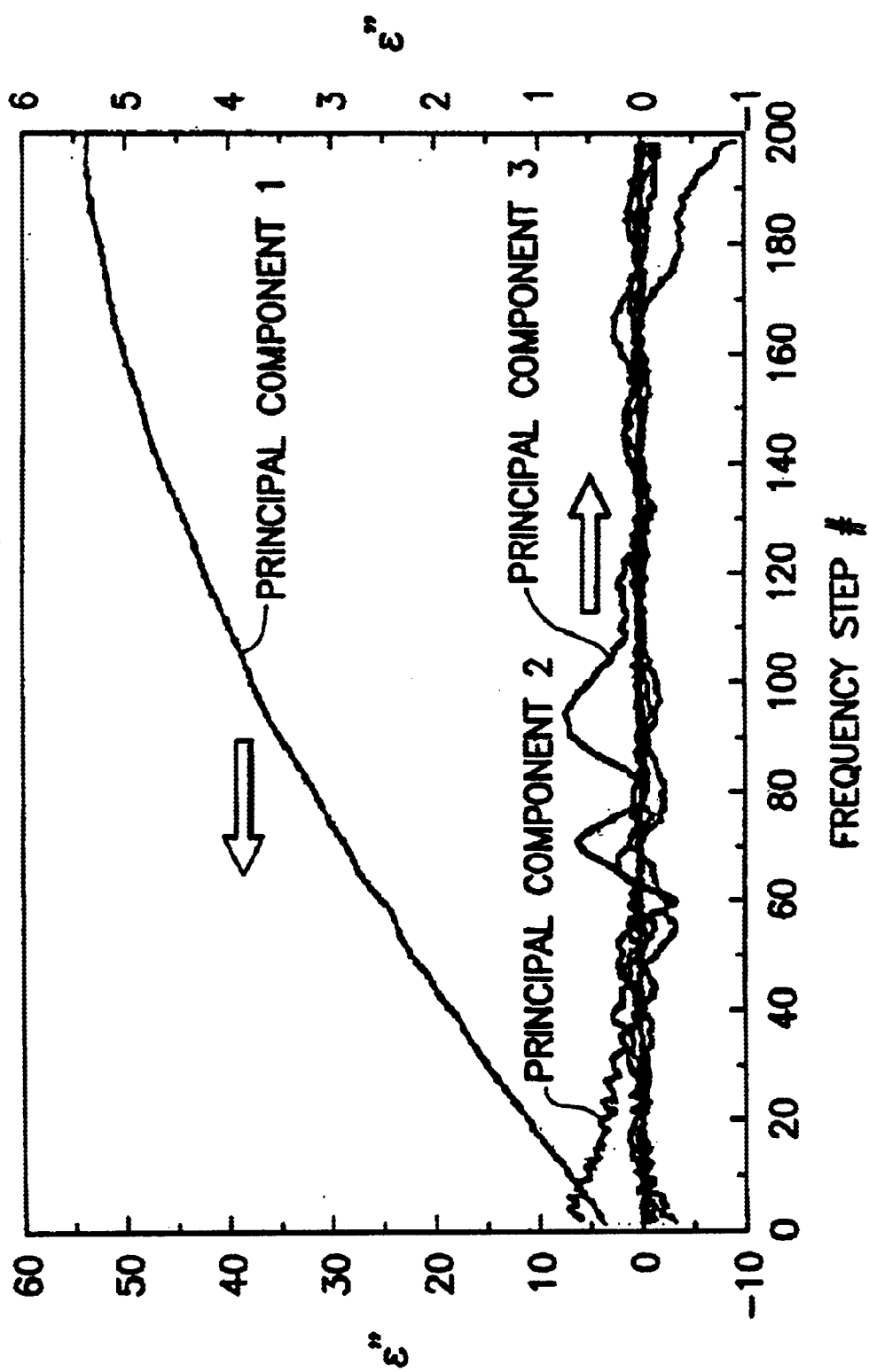
FIG. 6 shows a diagram that shows the principal components of the imaginary part ε"(f) of the dielectric constant.

FIG. 4 shows a table of the eigenvalues of the covariance matrix [Z'] (i.e. for the real part $\epsilon'$ of the dielectric constant) and [Z"] (i.e. for the imaginary part $\epsilon"$ of the dielectric constant). The eigenvalue spectrum is dominated by the eigenvalues 1 and 2, so that it can already be seen that at most two principal components (basis vectors) of the measured spectra carry information. FIG. 5 shows the weightings of the first three principal components. The weighting of the first basis vector decreases monotonically with the sample number, i.e. with an increasing oil volume ratio. The assigned basis vectors are represented in FIG. 6, the left-hand scale for $\epsilon"$ relating to the basis vector 1 and the right-hand scale for $\epsilon"$ relating to all the other basis vectors. It can already be seen from the typical dependency of the first basis vector, which essentially reflects the dipolar relaxation of water, but also from the size proportions of the first basis vector with respect to the other basis vectors, that the measured dielectric spectra of the reference emulsions are dominated by the basis vector 1. Accordingly, merely the basis vector 1 with its associated weighting will be used below for the further evaluation.

Figure 7:
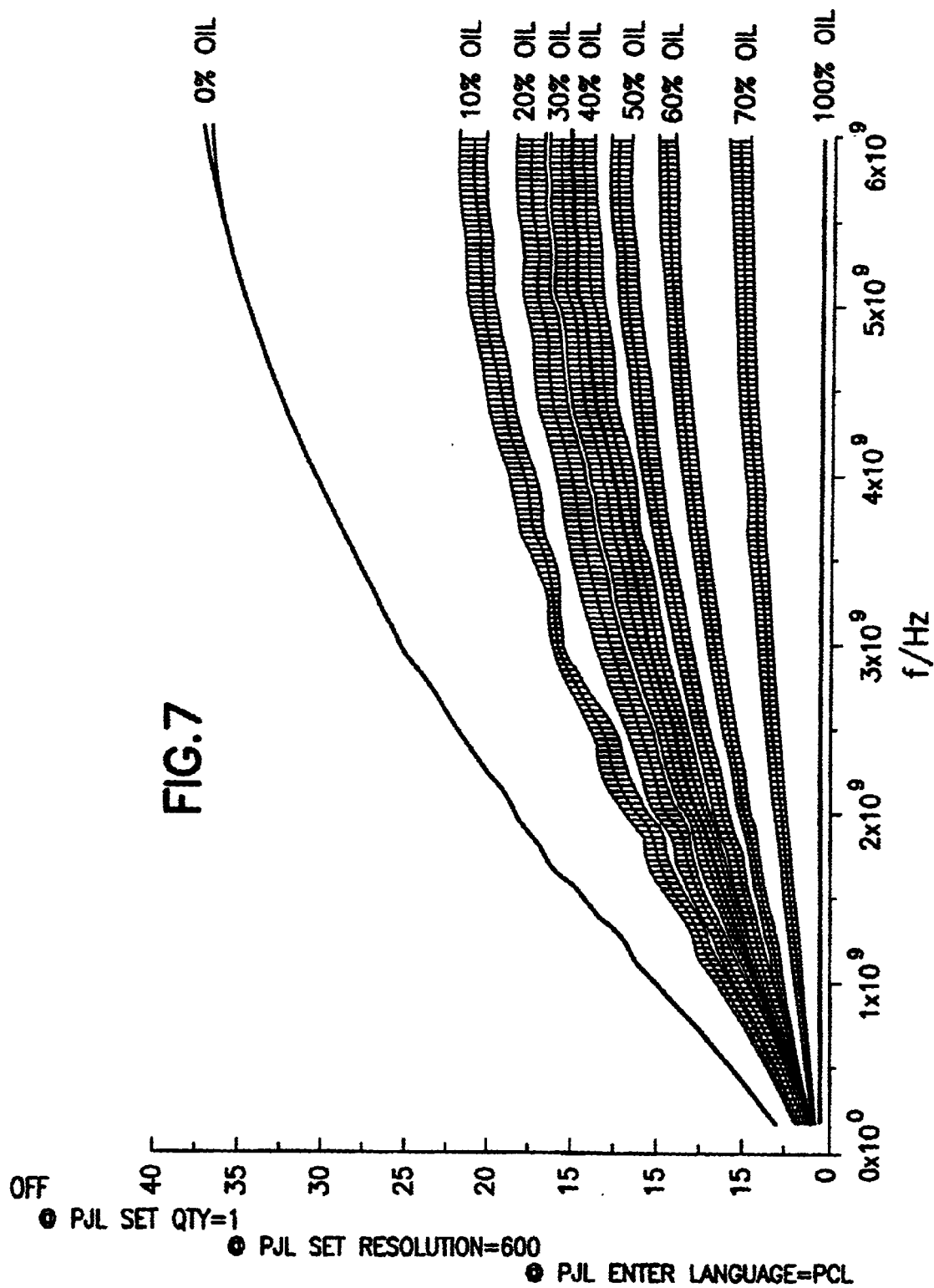
FIG. 7 shows a diagram that shows the measured frequency dependency of the imaginary part ε" of the reference emulsions, as well as dielectric spectra reconstructed from the first basis vector.
Figure 8:
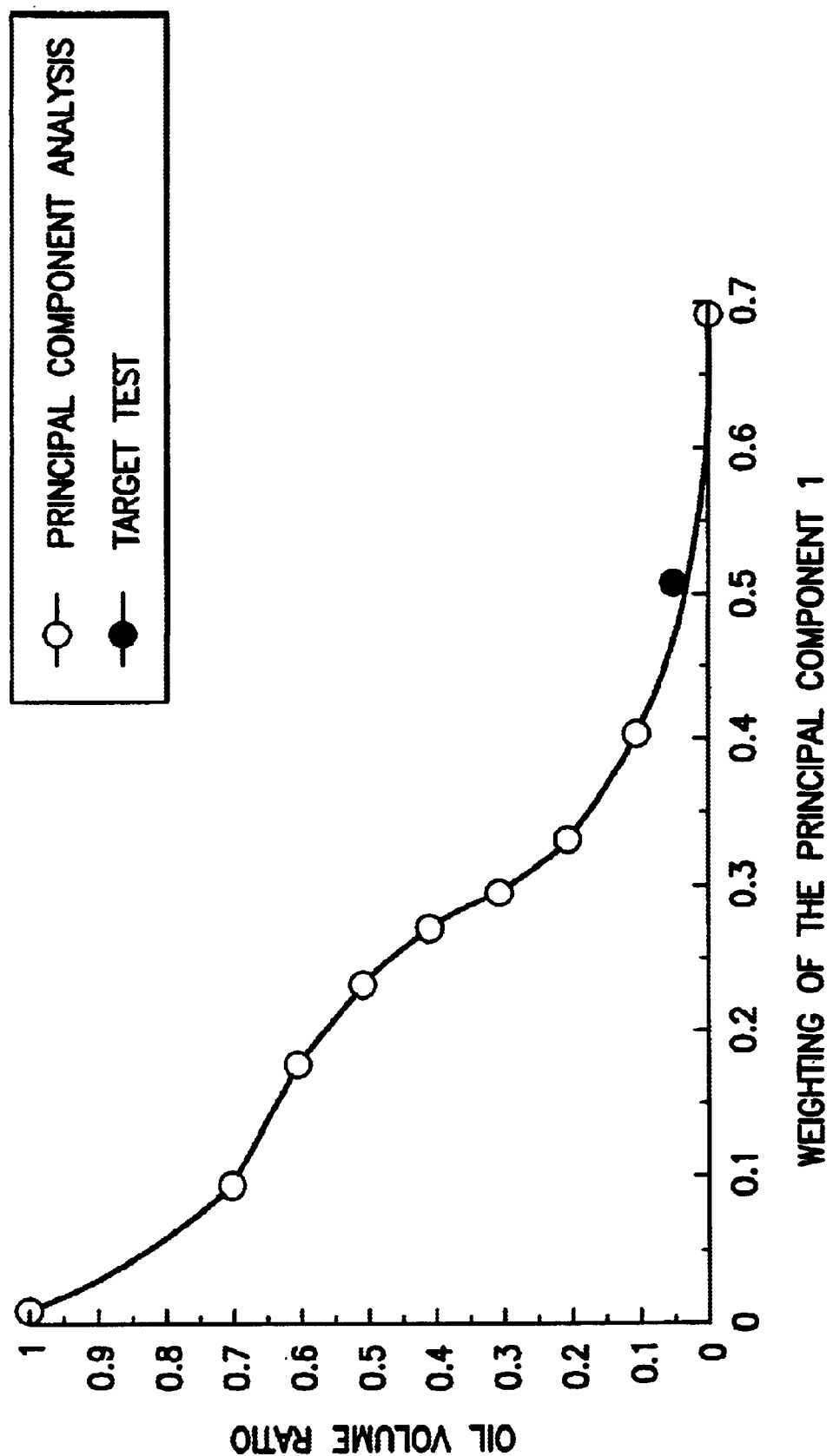
FIG. 8 shows a diagram that shows the oil volume ratio as a function of the weighting of the first basis vector, as well as the result of a target test procedure.

FIG. 7 represents the measured dielectric spectra ($\epsilon"(f)$) of the reference emulsions as well as the spectra reconstructed from the first basis vector. Other than for the dielectric spectra of the pure components (0% and 100% oil), the spectra reconstructed from the first basis vector lie fully within the error bars of the measurements. It can be concluded from this that the first basis vector with its associated weighting will provide sufficiently accurate calibration of the oil volume ratios. To that end, an empirical correlation between the oil volume ratio and the weighting of the first basis vector is determined, the result of which is represented in FIG. 8. A strictly monotonically decreasing relationship between the oil volume ratio and the weighting of the first basis vector is found. A spline interpolation through the values obtained by means of principal component analysis (open symbols) is further entered in FIG. 8.

Figure 9:
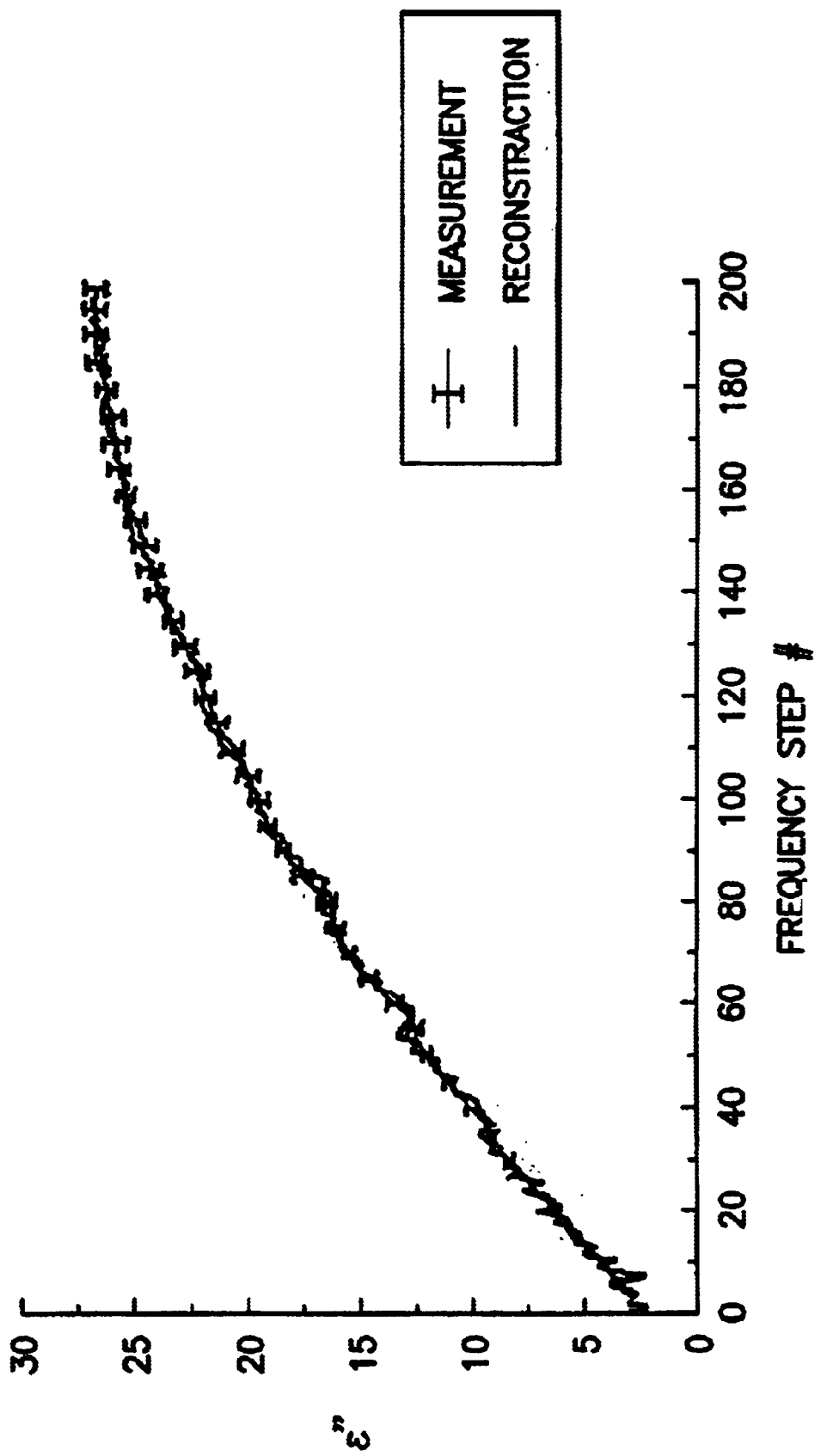
FIG. 9 shows a diagram that shows the frequency dependency of the imaginary part of the dielectric constant of a 5% by volume test emulsion, specifically in the form of a comparison of the measurement data with a reconstruction of the dielectric spectrum from the first basis vector.

The correlation between the oil volume ratio and the weighting of the first basis vector can be used as a measurement basis for the oil concentration of an unknown test emulsion. This is preferably done in the scope of a so-called target testing procedure, which is used to test whether a measured dielectric spectrum of the unknown test emulsion can be represented from the previously established basis vectors (in the present case, only the first basis vector) and which weightings are needed for this. As represented in FIG. 9, the dielectric spectrum ($\epsilon"$) of a 5% by volume O/W test emulsion is reproducible within the measurement errors using the first basis vector. To reconstruct the measured spectrum of this test emulsion, merely the basis vector 1 is therefore necessary. With the aid of the reconstruction represented in FIG. 9 of the dielectric spectrum of the test emulsion, it is possible to determine the weighting of the first basis vector that is needed for the reconstruction. This weighting of the first principal component is 0.51, and matches extremely well the spline interpolation of the already known weightings, as shown by FIG. 8. Therefore, the value of the oil concentration of the test emulsion determined by means of the method according to the invention is very close to the real value of 5%.

Figure 10:
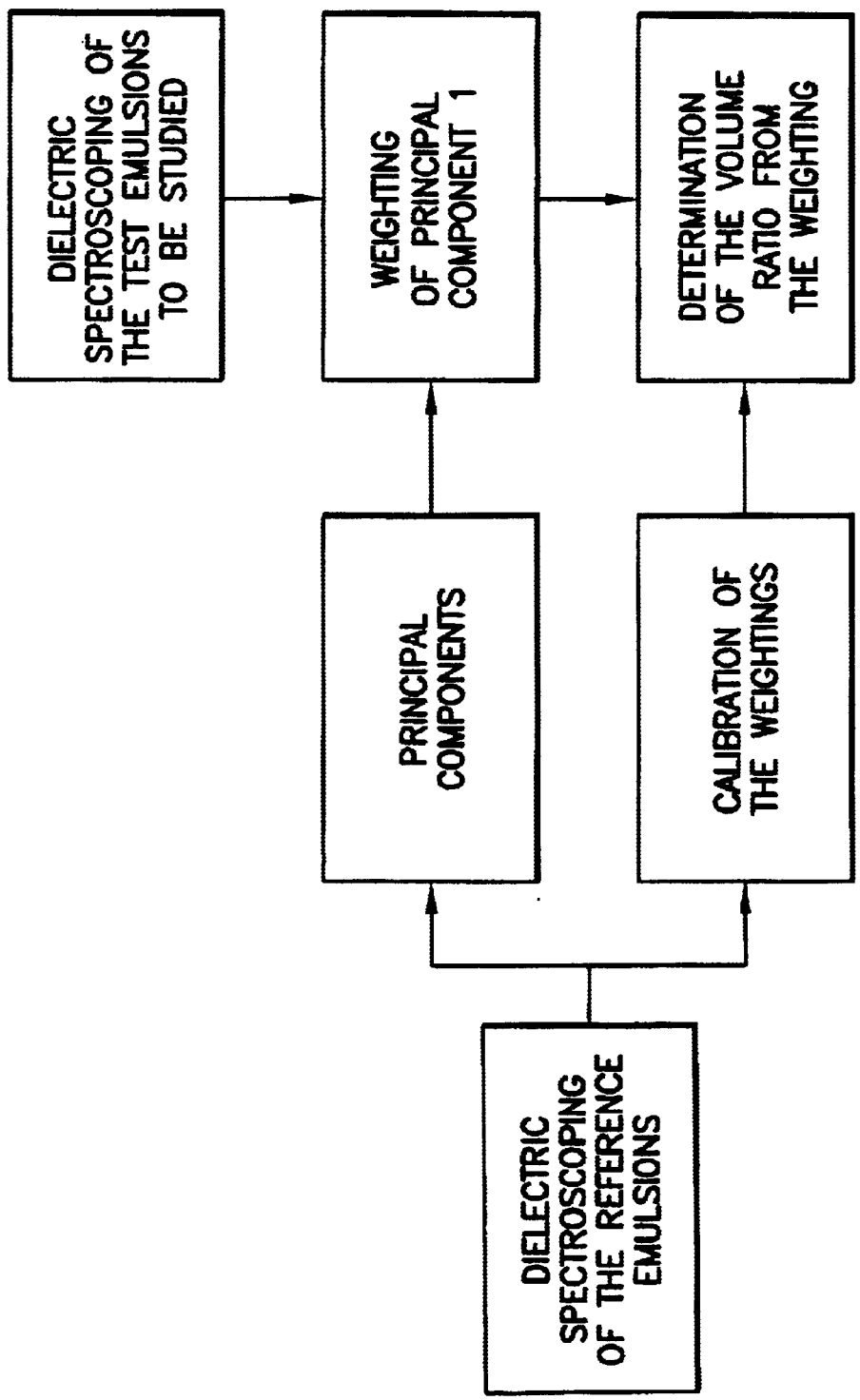
FIG. 10 shows a flow chart that shows the schematic procedure of the oil concentration determination.

The steps in the described embodiment of the method according to the invention can be represented summarily in the form of a flow chart that is shown in FIG. 10. First, the reference emulsions (reference substances) are dielectrically spectroscoped. It is sufficient to record merely the real or imaginary part of the dielectric constant. A redundant determination, in particular, which may for example be advantageous for checking the result, is possible if both the real and imaginary parts of the dielectric constant are determined. The dielectric spectra obtained of the reference emulsions are analyzed by means of principal component analysis in order to determine the principal components and their weightings. An empirical correlation between the weightings and the different concentrations of the reference emulsions is established. The test emulsions to be characterized are then dielectrically measured and analyzed by the described target testing procedure with the aid of the previously established basis vectors. The concentration of the test emulsion studied is deduced by the empirical correlation.

The method according to the invention, and the device according to the invention also permit simultaneous determination of several different properties, or material parameters, of test substances, since fundamentally differing properties of emulsions and/or suspensions and/or foams affect the complex dielectric functions (or impedance) thereof in different ways. For example, the described principal component analysis can be used to determine both the oil volume ratio and the drop size distribution, or the average drop size, of an oil-in-water emulsion at the same time. The method according to the invention allows quality features of emulsions and/or suspensions to be determined accurately, rapidly and automatically. The emulsions and/or suspensions and/or foams can, in particular, be studied over a wide range of compositions and drop or bubble sizes. When modern computers are used, the evaluation proceeds rapidly and can therefore also advantageously be used for process monitoring, control and/or regulation. Prior dilution of the substance to be studied is not necessary.

What is claimed is:

1. A method for determining at least one property of a test substance, the test substance being selected from the group consisting of a test emulsion, a test suspension and a test foam, and wherein the property influences a dielectric constant of the test substance, the property being selected from the group consisting of a volume ratio between disperse and continuous phases, a drop size distribution, an average size of foam bubbles or pores and viscosity of the test substance the method comprising the steps of preparing a test substance to be studied; establishing parts of the dielectric constant of the test substance at a plurality of frequencies; and determining the at least one property of the test substance by using the established parts.

2. The method of claim 1, wherein the property of the test substance is determined with the assistance of at least one reference substance, in which the at least one property to be determined is known.

3. The method of claim 2, having the further steps of: preparing the at least one reference substance; and establishing the real parts of the dielectric constant of the reference substance at a plurality of frequencies.

4. The method of claim 2, wherein a plurality of reference substances are prepared, which differ from one another and from the test substance at most in terms of the at least one property to be determined and consequent properties related thereto.

5. The method of claim 2, wherein the frequency lies in a range of from 1 MHz to 20 GHz.

6. The method of claim 2, wherein m reference substances $S_1, \ldots, S_m$ having assigned known properties $\phi_1, \ldots, \phi_m$ are prepared and the method comprises the further steps of:—establishing the parts $\epsilon"(\phi_i, f_j)$ of the dielectric constant of each of the reference substances $S_1, \ldots, S_m$ at n different frequencies $f_1, \ldots, f_n$;

forming a data matrix $D'=(\epsilon'(\phi_i,f_j))_{1\leq i\leq m; 1\leq j\leq n}$ having m columns and n rows;

wherein the property of the test substance is determined with the assistance of the data matrix $D'=(\epsilon'(\phi_i,f_j))_{1\leq i\leq m; 1\leq j\leq n}$.

7. The method of claim 6, having the further steps of: performing a principal component analysis of a data matrix $D'=R'\times C'$ to calculate the principal component matrix R' and a weighting matrix C' of the data matrix D' calculating a correlation between the weighting of at least the first principal component of the principal component matrix R' and the properties $\phi_1,\ldots,\phi_m$ of the reference substances $S_1,\ldots,S_m$; establishing the parts $\epsilon''(\phi_{test},f_j)$ of the dielectric constant of the test substance $S_{test}$ at the n different frequencies $f_1,\ldots,f_n$; calculating a weighting that is required for the at least first principal component of the principal component matrix R' to reproduce $\epsilon''((\phi_{test},f_j)$; and determining the property $\phi_{test}$ of the test substance from the calculated required weighting with the aid of the calculated correlation.

8. The method of claim 1, wherein the step of determining the property of the test substance and further comprises the step of monitoring the property during the production process.

9. A device for determining at least one property of a test foam as a test substance, the test substance being selected from the group consisting of a test emulsion, a test suspension and a test foam, and wherein the property influences a dielectric constant of the test substance, the property being selected from the group consisting of a volume ratio between disperse and continuous phases, a drop size distribution, an average size of foam bubbles or pores and viscosity of the test substance, comprising at least one measuring device for establishing parts of the dielectric constant of the test substance at a plurality of frequencies and an evaluation device that determines the at least the test substance by using the established parts.

10. The device of claim 9, wherein the evaluation device (18) determines the at least one property of the test substance with the assistance of at least one part of the dielectric constant of at least one reference substance, in which the at least one property to be determined is known.

11. The device of claim 10, wherein the measuring device is designed to establish the parts of the dielectric constant of the at least one reference substance.

12. The device of claim 10, wherein the measuring device comprises a network analyzer with an attached dielectric measuring head, designed to establish the parts of the dielectric constants of the test and reference substances in a frequency range of from 1 MHz to 20 GHz.

13. The device of claim 10, wherein the evaluation device and a substance production device that produces the test substance are in signal communication with a control device, and the control device is designed to monitor the substance production device while taking into account the test substance property determined by the evaluation device.

14. The use of a device as claimed in claim 9 for determining at least one of the volume ratio between disperse and continuous phases, the drop size distribution of the disperse phase, the average drop size of the disperse phase, the average size of the foam bubbles or pores and the viscosity of the test substance.

15. A computer-readable storage medium having a computer program stored thereon for determining at least one property of a test substance, the test substance being selected from the group consisting of a test emulsion, a test suspension and a test foam, and wherein the property influences a dielectric constant of the test substance and is selected from the group consisting of a volume ratio between disperse and continuous phases, a drop size distribution, an average size of foam bubbles or pores and viscosity of the test substance, the computer-readable storage medium has program parts for recording the parts of the dielectric constant of the test substance at a plurality of frequencies and for determining the at least one property of the test substance by using the established parts.

16. The computer-readable storage medium of claim 15, wherein the property of the test substance is determined with the assistance of at least one part of at least one reference substance, in which the at least one property to be determined is known.

17. A method for determining at least one property of a test substance selected from the group consisting of a test emulsion, a test suspension and a test foam, wherein the property influences a dielectric constant of the test substance and is comprising the steps of: preparing a test substance to be studied; establishing at least one of the real and imaginary part(s) of the dielectric constant of the test substance at a plurality of frequencies; and determining the at least one property of the test substance by using the at least one established real and imaginary part(s), wherein the property of the test substance is determined with the assistance of at least one real and/or imaginary part of the dielectric constant of at least one reference emulsion and of at least one reference suspension and of at least one reference foam as at least one reference substance, in which the at least one property to be determined is known, and wherein the test substance property to be determined is the volume ratio between disperse and continuous phases, the drop size distribution of the disperse phase, the average drop size of the disperse phase, the average size of the foam bubbles or pores and the viscosity of the test substance.

18. A device for determining at least one property of a test substance selected from the group consisting of a test emulsion, a test suspension and a test foam, wherein the property influences a dielectric constant of the test substance and is different than the dielectric constant, the device comprising at least one measuring device for establishing at least one of the real and imaginary part(s) of the dielectric constant of the test substance at a plurality of frequencies and an evaluation device that determines the at least one property of the test substance by using the established real and imaginary part(s), wherein the evaluation device determines the at least one property of the test substance with the assistance of at least one real and imaginary part of the dielectric constant of at least one reference emulsion and of at least one reference suspension and of at least one reference foam as at least one reference substance, in which the at least one property to be determined is known, and wherein the test substance property to be determined is selected from the group consisting of the volume ratio between disperse and continuous phases, the drop size distribution of the disperse phase, the average drop size of the disperse phase, the average size of the foam bubbles or pores and the viscosity of the test substance.

* * * * *